(12) United States Patent
McConnell et al.

(10) Patent No.: US 10,416,175 B2
(45) Date of Patent: Sep. 17, 2019

(54) OPIOID DETECTION

(71) Applicant: Randox Laboratories Limited, Crumlin (GB)

(72) Inventors: Ivan McConnell, Crumlin (GB); Elouard Benchikh, Crumlin (GB); Philip Lowry, Crumlin (GB); Peter Fitzgerald, Crumlin (GB)

(73) Assignee: Randox Laboratories Limited, Crumlin (GB)

( * ) Notice: Subject to any disclaimer, the term of this patent is extended or adjusted under 35 U.S.C. 154(b) by 155 days.

(21) Appl. No.: 15/385,063

(22) Filed: Dec. 20, 2016

(65) Prior Publication Data

US 2017/0176476 A1 Jun. 22, 2017

(30) Foreign Application Priority Data

Dec. 21, 2015 (GB) .................................. 1522510.5

(51) Int. Cl.
*G01N 33/94* (2006.01)
*C07K 16/44* (2006.01)
*G01N 33/543* (2006.01)

(52) U.S. Cl.
CPC ......... *G01N 33/9486* (2013.01); *C07K 16/44* (2013.01); *G01N 33/54366* (2013.01); *C07K 2317/33* (2013.01)

(58) Field of Classification Search
CPC ................ C07K 16/44; C07K 2317/33; G01N 33/54366; G01N 33/9486
See application file for complete search history.

(56) References Cited

U.S. PATENT DOCUMENTS 9,952,206 B2 * 4/2018 Benchikh ........... G01N 33/5308

FOREIGN PATENT DOCUMENTS

EP        1988398 A1    11/2008
WO   2008/009962 A1     1/2008

OTHER PUBLICATIONS

Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
Szurdoki et al., "Important Factors in Hapten Design and Enzyme-Linked Immunosorbent Assay Development," in Immunoanalysis of Agrochemicals; Nelson, J., et al.; ACS Symposium Series, 1995, vol. 586, Chapter 4, pp. 39-63.*
Englebienne, "Immune and Receptor Assays in Theory and Practice," CRC Press, 2000, p. 308.*
Alpha Diagnostic International, Product Data Sheet, Cat# 700-101, "Keyhole limpet hemocyanin (KLH, hemocyanin) coated ELISA plates," posted on Internet Apr. 10, 2013.*
Kronstrand et al., "Unintentional fatal intoxications with mitragynine and O-desmethyltramadol from the herbal blend Krypton," J. Anal. Toxicol., 2011, vol. 35, No. 4, pp. 242-247.*
Grond, S., et al., Clinical Pharmacology of Tramadol, Clin Pharmacokinet., 2004, vol. 43, No. 13, pp. 879-923.
Tramadol, Randox Toxicology, Randox Laboratories Ltd., 2016, 5 pages. https://www.randoxtoxicology.com/products/elisa/tramadol/.

* cited by examiner

*Primary Examiner* — Galina M. Yakovleva
(74) *Attorney, Agent, or Firm* — Gavrilovich, Dodd & Lindsey LLP

(57) ABSTRACT

An immunoassay method is described which detects O-desmethyltramadol only. This enables an assay of high sensitivity and specificity avoiding false positive results. The unique antibodies incorporated in the immunoassay method can be combined with antibodies which detect mitragynine to provide an assay which increases the possibility of detecting the commonly found drug combination of O-desmethyltramadol and mitragynine.

6 Claims, 2 Drawing Sheets

OPIOID DETECTION

CROSS-REFERENCE TO RELATED APPLICATIONS

The instant application claims the benefit of priority under 35 USC § 119 to United Kingdom Application No. 1522510.5, entitled "OPIOID DETECTION" filed 21 Dec. 2015, the entire contents of which are incorporated herein by reference in their entirety.

BACKGROUND TO THE INVENTION

Tramadol, systematic name (±)-cis-2-[(dimethylamino) methyl]-1-(3-methoxyphenyl)cyclohexanol hydrochloride, is a widely prescribed centrally acting analgesic, administered as a racemic mixture, for the treatment of moderate to severe pain. Acting weakly at the μ-opioid receptor it has been shown to be addictive and provoke abusive behaviour. Following oral administration its major metabolites are (±)-cis-2-[(methylamino)methyl]-1-(3-methoxyphenyl)cyclohexanol trivial name: N-demethyltramadol/N-desmethyltramadol (NDT) and (±)-cis-2-[(dimethylamino)methyl]-1-(3 hydroxyphenyl)-cyclohexanol trivial name: O-desmethyltramadol/O-demethyl-tramadol (ODT). Urinary excretion of tramadol shows wide inter-individual variation; reported excretory amounts for tramadol and the two main metabolites over 24-72 hours of: tramadol 12-32%, N-desmethyltramadol 2-31% and O-desmethyltramadol 5-15% (Grond and Sablotzki 2004). O-desmethyltramadol is a considerably more potent μ-opioid agonist than the parent drug tramadol and it has recently been found in legal herbal products under names such as "Krypton". Abuse and reports of fatalities connected to O-desmethyltramadol intake make its analytical detection for toxicological purposes desirable, especially using the practical and relatively inexpensive immunoassay technology. To date immunoassays have emphasised the detection of parent and metabolites (Table 1).

TABLE 1

Cross-reactivity and sensitivity ($IC_{50}$ in ng/ml) comparisons of Tramadol commercial immunoassays

| Analyte | Randox | Bio-Quant | Immunanalysis | Neogen | IDS |
|---|---|---|---|---|---|
| | | | % Cross-reactivity | | |
| Tramadol | 100 | 13 | 100 | 100 | 100 |
| NDT | 4 | <5 | 44 | 6 | <2 |
| ODT | 57 | 100 | 6 | 27 | 40 |
| Sensitivity | 0.2 | 75 | 200* | 5 | 200* |

*cut-off value

EP1988398 describes a method for the detection of tramadol, N-desmethyltramadol and O-desmethyltramdol, the assay being specific to tramadol with cross-reactivity to N-desmethyltramadol and O-desmethyltramdol,

SUMMARY OF THE INVENTION

The invention describes immunoassay methods that detect O-desmethyltramadol but that do not detect tramadol or N-desmethyltramadol. Further described are antibodies which bind to O-desmethyltramadol but exhibit negligible binding to tramadol and N-desmethyltramadol. Substrates and kits comprising the antibodies are also described.

The invention described an immunoassay method for detecting O-desmethyltramadol, the method comprising: i. contacting a solution or in vitro sample with a detecting agent and an antibody, wherein the antibody has a cross-reactivity of less than 5% to each of tramadol and N-desmethyltramadol compared with a cross-reactivity of 100% to O-desmethyltramadol; ii. detecting either the presence and/or amount of detecting agent bound to the antibody or the presence and/or amount of detecting agent not bound to the antibody; and iii. determining the presence and/or amount of O-desmethyltramadol.

The invention also describes an antibody having less than 5% cross-reactivity to each of N-desmethyltramadol and tramadol compared to a cross-reactivity of 100% to O-desmethyltramadol.

The invention further described an immunogen of structure 1A:

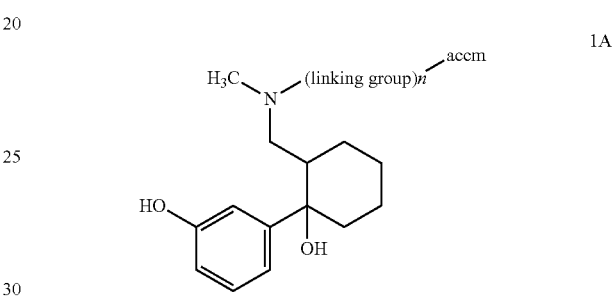

wherein: n=0 or 1; and accm is an antigenicity conferring carrier material. The invention also described antibodies raised against such an immunogen.

DETAILED DESCRIPTION OF THE INVENTION

Immunoassay Method

Figure 1:
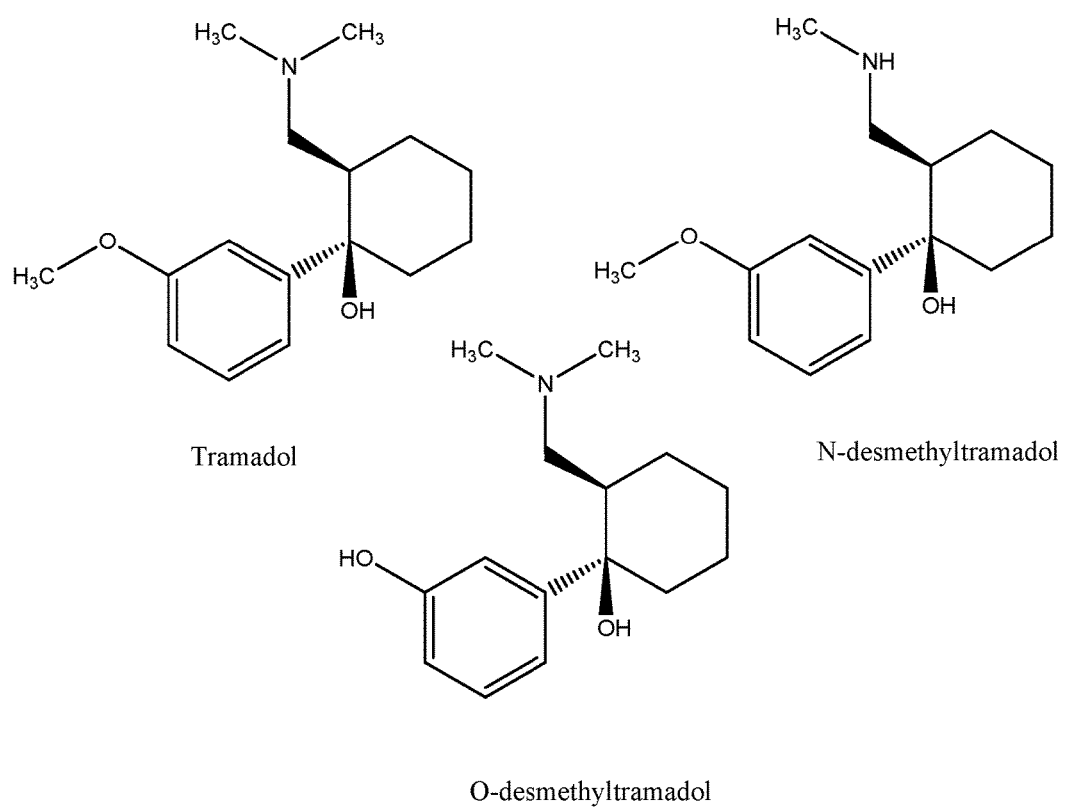
FIG. 1 shows the structures of Tramadol, O-desmethyltramadol and N-desmethyltramadol.

The invention describes an immunoassay method for detecting O-desmethyl-tramadol in a solution or an in vitro sample from a subject, the method comprising contacting a detecting agent and an antibody of the invention with the solution or in vitro sample and detecting the presence and/or amount of O-desmethyltramadol. In one embodiment, the detecting agent competes with O-desmethyltramadol present in the sample for binding to the antibody.

For purposes of comparison, one analyte with high cross-reactivity is generally given a value of 100%, with all other analytes accorded a value relative to this; in addition, as is known by one skilled in the art, for cross-reactivity to be of practical use the analyte-specific antibody must display a high sensitivity as measured by a suitable metric such as the $IC_{50}$. The $IC_{50}$ is a commonly used indicator of antibody sensitivity for immunoassays.

the invention further describes an immunoassay method for detecting O-desmethyl-tramadol comprising bringing a sample suspected of containing O-desmethyl-tramadol into contact with a detecting agent and an antibody specific to O-desmethyltramadol, in which the detecting agent competes with O-desmethyl-tramadol present in the sample for binding to the antibody characterised in that the antibody specific to O-desmethyltramadol has a cross-reactivity of less than 5%, preferably less than 2%, to each of tramadol and N-desmethyltramadol; most preferably the antibody specific to O-desmethyltramadol has a cross-reactivity of less than 1% to each of tramadol and N-desmethyltramadol i.e. less than 1% cross-reactivity to tramadol and less than 1% cross-reactivity to N-desmethyl-tramadol.

The invention further describes an immunoassay method for detecting O-desmethyl-tramadol in a solution or an in vitro sample from a subject, the method comprising contacting a detecting agent and an antibody of the invention with the solution or in vitro sample and detecting the presence and/or amount of O-desmethyltramadol, characterised in that the antibody specific to O-desmethyltramadol has a cross-reactivity of less than about 5%, preferably less than about 2%, to each of tramadol and N-desmethyltramadol compared with 100% cross-reactivity to O-desmethyltramadol; most preferably the antibody has a cross-reactivity of less than about 1% to each of tramadol and N-desmethyltramadol i.e. less than about 1 cross-reactivity to tramadol and less than about 1% cross-reactivity to N-desmethyltramadol compared with 100% cross-reactivity to O-desmethyltramadol.

As used herein, "about" is to account for such instances as slight measurement variations which occur within scientific measurement due to inter-individual and equipment variation in each scientific procedural step, as well as mathematically based variation in result reporting which can incorporate numerical 'rounding-down' or 'rounding-up' operations.

As used herein, an antibody "specific" to a particular molecule shows the greatest binding to that molecule compared to other molecules as measured by a recognised metric such as the limit of detection, limit of quantification or the $IC_{50}$.

As used herein, "detecting" includes qualitative detection i.e. presence or absence without quantification, semi-quantitative detection i.e. presence or absence of a pre-specified amount, and quantitative detection i.e. the amount of the substance is quantified.

To enable the assay to be effectively applied, an antibody with an $IC_{50}$ of less than or about 1 ng/ml, preferably less than or about 0.5 ng/ml, more preferably less than or about 0.25 ng/ml for O-desmethyltramadol is preferred. In the embodiment the $IC_{50}$ of the antibody to O-desmethyltramadol is less than or about 1 ng/ml; the qualification of the $IC_{50}$ value in ng/ml using the word "about" is to account for such instances as slight measurement variations which occur within scientific measurement due to inter-individual and equipment variation in each scientific procedural step, as well as mathematically based variation in result reporting which can incorporate numerical 'rounding-down' or 'rounding-up' operations.

It is common practice that in the immunoassay method the presence or amount of target analyte(s) is gauged by reference to one or more calibrator values usually in the form of a cut-off value or calibration curve; using a calibrator to construct a calibration curve or 'standard curve' which allows the sensitivity (in this case the $IC_{50}$) and cross-reactivity of antibodies to the target analytes to be derived. However, it is possible that detection of the signal originating from the detecting agent does not make use of a calibrator—this possibility applies to the method of the invention.

A calibrator is well known in the art and refers to a reference value or values, the reference being a substance which enables a threshold concentration or the exact or calibrator equivalent amount of analyte(s) to be determined. The determination of an exact or calibrator equivalent amount of analyte(s) usually requires the construction of a calibration curve (also known as a standard curve). The number of calibrator points can vary, but is usually from 5 to 9. To enable a practical assay for clinical/commercial use, the binding of the antibody to the analyte(s) must be such that the concentration at which the analytes are detected is at an acceptable level. The detecting agent (also known as a tracer or conjugate) is the substance which emits a detectable signal and comprises a moiety of similar structure to a target analyte conjugated, by way of a linking group, to a labelling agent, that is able to bind to one of the antibodies of the invention.

In one embodiment, the presence of detecting agent linked to the antibody can be detected in between about 10 hours and about 1 minute, between about 2 hours and about 10 minutes, between about 1 and a half hours and about ten minutes, or between about 1 hour and 20 minutes. In yet another embodiment, the presence of detecting agent linked to the antibody can be detected within about 30 minutes.

The term "subject" refers to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In one embodiment, the subject is a non-human animal such as a farm animal (e.g., a horse, cow, pig or sheep), or a pet (e.g., a dog, cat, guinea pig or rabbit). In another embodiment, the subject is a "human".

The term "biological sample", as used herein, includes, without limitation, cell cultures or extracts thereof; biopsied material obtained from a mammal or extracts thereof; blood, saliva, urine, faeces, semen, tears, or other body fluids or extracts thereof. In one embodiment, the biological sample is a peripheral biological fluid, but is including whole blood, serum, plasma, hair or urine. The sample may also be a solution which is suspected of containing a drug. An in vitro sample is any suitable biological sample such as, but not limited to, blood, serum, plasma, urine or saliva. The in vitro sample is preferably a serum, plasma or urine sample. The solution can be a liquid suspected of containing one or more of these drugs. Alternatively, as these drugs can be in tablet or plant form e.g. sold as a herbal product, analysis of drugs suspected of containing these psychoactive ingredients may require pre-treatment to achieve a formulation suitable for analysis, such as dissolution in a suitable liquid.

The immunoassay method format of the invention is commonly referred to as a competitive assay and is well known in the art. Due to inter-molecular attractive forces such as hydrogen bonding and van der Waal's forces there is often a degree of binding or affinity between two molecules whatever their respective structures; the skilled person recognizes that no cross-reactivity or minimal cross-reactivity implies that in the context of a working immunoassay any binding or interaction between an antibody and non-target analytes is at such a low level that it does not compromise the integrity or aim of the immunoassay i.e. false positives are avoided. There are several parameters that can be used to compare the relative degree of binding of an antibody to different analytes including the lowest limit of detection (LOD), the lowest limit of quantification (LOQ) and the $IC_{50}$. The $IC_{50}$ is determined using a competitive assay (see Example 11 of the General Method, Examples and Results section and Table 2) and can be used to derive analyte cross-reactivities.

The detecting agent used in the method of the invention is a species which comprises a moiety which is able to bind to the antibody as well as a detectable label. A detectable label includes enzymes able to promote light emission from a substrate—the moiety is preferably attached to the detectable label by a linking group. The moiety able to bind to the antibody is preferably a structure based on O-desmethyltramadol; a preferred detecting agent is described in Example 10 of the Examples section, but it would be appreciated by the skilled person that the linking groups and detectable labels of the detecting agent can be varied without affecting the practical application of the immunoassay method of the invention. For example, the detecting agent that can be used in the immunoassay method of the invention can be based on a compound of Structure 1 in which the linking group is attached to a detectable label such as horseradish peroxidase, the detectable label replacing the antigenicity conferring carrier material (accm), as described below.

The antibodies of the immunoassay method of the invention are preferably located at the surface of a substrate such as a biochip, a microtitre plate or a bead, although it is recognised in the art that the competitive immunoassay method format allows antibodies to be in solution.

Kits

The invention further describes a kit comprising an antibody of the invention and optionally a detecting agent. The kit can also be presented with the antibodies passively adsorbed on or chemically bonded to a solid state device.

Substrates

A solid state device may also be referred to as a substrate. Another aspect of the invention is a substrate which supports the antibodies of the invention, and are useful in the methods and kits of the invention. The antibodies engage (are bound or linked to) with the substrate by, for example, passive adsorption or can be chemically bonded to the substrate attached by way of, for example, covalent bonds. Such covalent bonding generally requires the initial introduction of a chemically active compound covalently attached to the substrate surface prior to antibody addition. The antibody itself may also require the addition of a chemical activating group to achieve substrate bonding. These requirements are well known in the art. The substrate can be any medium capable of adsorbing or bonding to an antibody, for example a bead, a microtitre plate or a nanoparticle (optionally chemically-activated), but is preferably of a planar conformation (optionally chemically-activated) such as a glass slide or a biochip. A biochip or microtitre plate are the preferred substrates.

A biochip is a thin, wafer-like substrate with a planar surface which can be made of any suitable material such as glass or plastic but is preferably made of ceramic. The biochip is able to be chemically-activated prior to antibody bonding or is amenable to the passive adsorption of antibodies.

The skilled person in biochip development for immunoassay application will recognize that a planar surface at high resolution e.g. if using a scanning electron microscope, is not perfectly 'flat' but will possess an uneven surface, the important aspect being that the 'approximately' planar surface is suitable for application. A microlayer coating of material can optionally be added to the planar surface of the substrate either prior to or after antibody placement. Either the upper surface or both surfaces of the substrate can be coated. The biochip can be integrated into or placed into a device with walls. Such a walled device can aid in the retention of added sample or solution.

The solid state device can also support other antibodies which have a binding specificity which is different from the binding specificity of the antibodies of the invention. Such a support with multiple different antibodies is often described as a multianalyte array (reference to an 'array' includes a microarray). If the method of detection is different fluorescent labels, each different fluorescent label emitting electromagnetic radiation at a unique wavelength, then the location of placement of the antibodies on the solid substrate is not critical. However, for antibodies forming part of a multianalyte array in which the detecting agent is, for example, a chemiluminescent molecule, the antibodies of differing specificity must not overlap and must be located in discrete areas on the solid state device. Such a system is also referred to as a spatially addressable multianalyte array.

Immunogens

A further aspect of the invention describes immunogens of the invention, including immunogens useful in the preparation of antibodies of the invention of Structure 1 or 1A

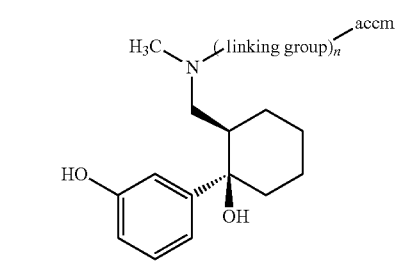

Structure 1

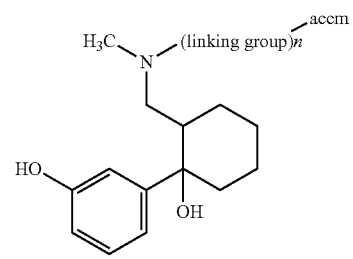

Structure 1A

In which n=0 or 1 and the linking group if present joins the N atom to the antigenicity conferring carrier material (accm). The linking group or linker, if present, links the N atom to the accm and can be any appropriate acyclic or cyclic system or a combination of cyclic and acyclic systems.

In one embodiment, the linking group is a substituted or unsubstituted alkanediyl, alkenediyl, arylene, cycloaliphatic, heterocycle or combinations of thereof. In another embodiment, the linking group is —$(CH_2)_{n'}$—CO—; and n'=1-5.

Antibodies

A further aspect of the invention describes antibodies of the invention, including antibodies useful in the methods of the invention and in the kits of the invention, which have been derived or are raisable from an immunogen of Structure 1 or 1A

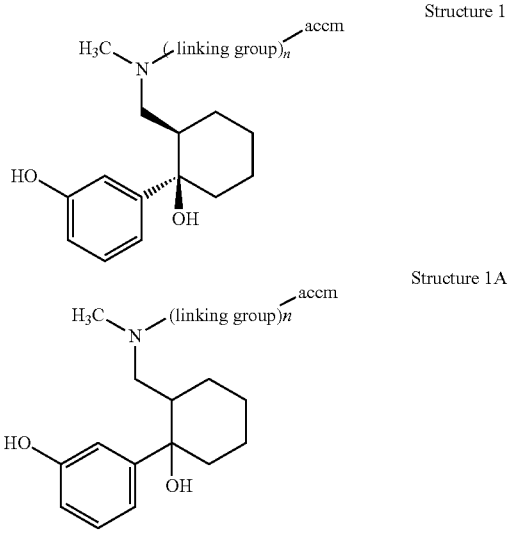

Structure 1

Structure 1A

In which n=0 or 1 and the linking group if present joins the N atom to the antigenicity conferring carrier material (accm). The linking group or linker, if present, links the N atom to the accm and can be any appropriate acyclic or cyclic system or a combination of cyclic and acyclic systems.

In one embodiment, the linking group is a substituted or unsubstituted $C_{1-10}$ alkanediyl, $C_{1-10}$ alkenediyl, arylene, cycloaliphatic, heterocycle or combinations of thereof. In another embodiment, the linking group is —$(CH_2)_{n'}$—CO—; and n'=1-5.

The invention also describes an antibody which binds specifically to O-desmethyl-tramadol and shows less than about 5% cross-reactivity to each of N-desmethyltramadol and tramadol compared to a cross-reactivity of about 100% to O-desmethyltramadol. The antibody is further characterised by having an $IC_{50}$ of less than or about 1 ng/ml to O-desmethyltramadol.

The antibodies of the invention can be used in the immunoassay methods and kits of the invention as described herein.

The term "antibody" as used herein refers to an immunoglobulin or immunoglobulin-like molecule. In a one embodiment, the antibodies are monoclonal or polyclonal antibodies. However, the skilled person will understand that any type of immunoglobulin molecule or fragment thereof can be used, for example, Fab fragments, scFv fragments and any other antigen binding fragments all of which fall within the scope of the current invention. The antibodies may be produced by any method as known to those skilled in the art. Any suitable host animal may be used in the immunisation process including a mammalian animal for example, but not limited to, sheep, rabbit, mouse, guinea pig or horse. In addition, the antibodies may be in the form of polyclonal antisera.

The term "raisable" means that the antibody can be raised from an immunogen of the current invention but is not necessarily so raised. In this context, "raisable" includes, but is not limited to, "raised". In relation to the antibodies described herein, in the context of the current invention, 'raised' is synonymous with 'derived'.

The phrase "an antibody which binds or specifically binds to an epitope of structure . . . " implies that the antibody, if polyclonal, will comprise clones whose high concentration and binding characteristics ensure an assay incorporating the antibody will bind to and ultimately support the identification of the compound of interest. Alternatively, the antibody could be a monoclonal antibody specific for a particular structural part of or the whole of the compound.

The terms "binds", "able to bind to" or "capable of binding" as used herein means that under standard immunoassay conditions, for example as described in 'Immunoassay: A practical guide' by Brian Law, Taylor and Francis Ltd (ISBN 0-203-48349-9), the antibodies will bind to said molecules.

The linking group, which is standard in the art, can be any conventional linking group conventionally used in this field. The term "linking group" as used herein is any bifunctional molecule able to covalently join two groups, for example, the N atom of Structure 1 to an accm. The linking group is ideally a functionalised linking group joining the accm to the N atom. In one embodiment, the linking group can be a short chain saturated or unsaturated, substituted or unsubstituted alkanediyl or alkenediyl chain of 1-10 carbon atoms, or arylene groups, or saturated or unsaturated cycloalkanes (cycloaliphatics), or heterocycles or combinations of alkanediyl, alkenediyl, arylene groups, saturated or unsaturated cycloalkanes and heterocycles optionally supporting a functional group (e.g. carboxy, amino, carbonyl) at the chain or ring end(s) following or preceding attachment to N or the accm. In one embodiment, the linking group is a substituted or unsubstituted alkanediyl, alkenediyl, arylene, cycloaliphatic, heterocycle or combinations of thereof. In another embodiment, the linking group is —$(CH_2)_{n'}$—CO—; and n'=1-5. The total linear chain length of the linker is preferably 1-10 atoms, most preferably 1-6 atoms. In the context of the invention, the phrase 'total linear chain length' in conjunction with 1-10 atoms or 1-6 atoms, implies that, if a ring system is present in the linker, it is afforded the value of one atom i.e. a benzene ring and a cyclohexane ring in the linker corresponds to 2 atoms and diphenylmethane (phenyl-CH$_2$-phenyl) corresponds to 3 atoms. Preferably the immunogen from which the antibody is raised has a linking group that is a $C_{1-10}$, preferably a $C_{1-6}$ substituted or unsubstituted alkanediyl or arylene moiety with a functional group at the end of the linking group which attaches to the accm.

The term "functional group" is a standard phrase in the chemistry field and refers to a reactive group such as an amine, ketone, ether, thioether, amide, alkene, thiol, ester, carboxylic acid or aldehyde. In one embodiment, the functional groups is an amine, ketone, or ester. In one embodiment, the functional group is a ketone.

In a preferred embodiment, the linker is of structure 1 is —$(CH_2)_{n'}$—CO— in which n'=1-5, more preferably n'=3.

Numerous accms are useable in the invention but are preferably selected from keyhole limpet haemocyanin (KLH), bovine thyroglobulin (BTG), bovine serum albumin (BSA), egg ovalbumin (OVA), bovine gamma globulin or cationised BSA (cBSA)—see Standard Reagents, Standard Methods, Examples and Results for further examples.

Figure 2:
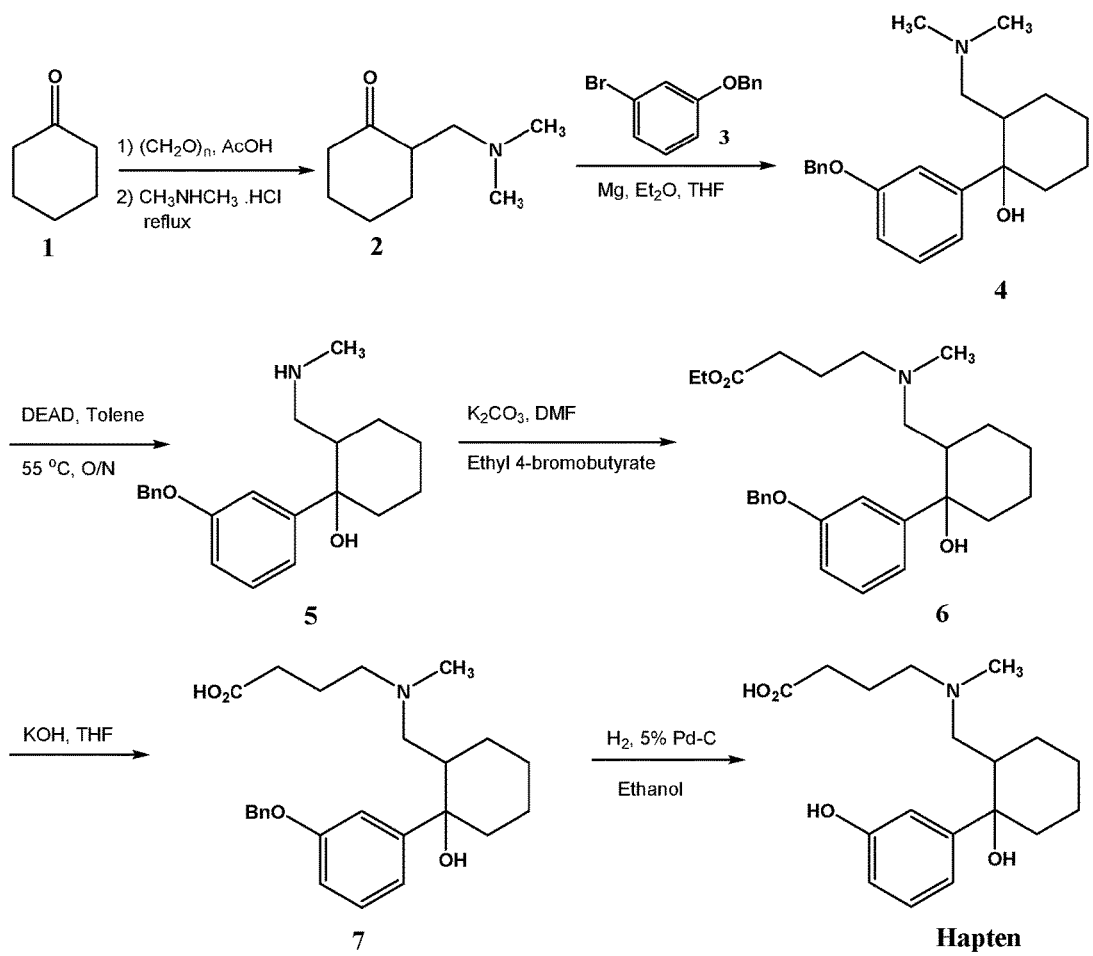
FIG. 2 shows the synthesis of Hapten; Bn is benzyl.

Antigenicity conferring carrier materials are well known in the art and can be any material that makes all or part of the hapten (as used herein the "hapten" is a pre-immunogenic molecule or 'small molecule' that stimulates antibody production only when linked to a larger carrier molecule such as an accm—an example in the case of the current invention is the Hapten exemplified in Example 7 and FIG. 2. Once the hapten is linked to the accm, it forms the immunogen) immunogenic, such as a protein, a protein fragment, a synthetic polypeptide or a semi-synthetic polypeptide. The process of immunogen formation generally involves coupling of a hapten to a linking agent, the latter subsequently coupled to an accm. Numerous linking groups (also known as linkers or crosslinkers) and accms are commercially available and have been described in the literature (Thermo Scientific Crosslinking Technical Handbook, 1606073 April 2009; Bioconjugate Techniques G. Hermanson, ed, Academic Press, 1996, 785 pp).

As used herein the term "linked" is synonymous with bound, attached, conjugated, crosslinked, or coupled, and means bound or linked or attached by covalent or non-covalent bonds or by active or passive adsorption or absorption.

The term "alkyl" as used herein means a saturated straight or branched chain hydrocarbon.

The term "alkanediyl" and "alkylene" are interchangeable and as used herein, represent a saturated divalent straight or branched chain hydrocarbon group and is exemplified by methylene, ethylene, isopropylene and the like.

The term "alkenediyl" and "alkylenylene" are interchangeable and as used herein, represent a divalent straight or branched chain hydrocarbon group with at least one double bond and is exemplified by methylene, ethylene, isopropylene and the like.

The term "cycloaliphatic" (or "carbocycle" or "carbocyclyl" or "carbocyclic" or saturated or unsaturated cycloalkyl") refers to a non-aromatic carbon only containing ring system which can be saturated or contains one or more units of unsaturation, having three to fourteen ring carbon atoms. In some embodiments, the number of carbon atoms is 3 to 10. In other embodiments, the number of carbon atoms is 4 to 7. In yet other embodiments, the number of carbon atoms is 5 or 6. The term includes monocyclic, bicyclic or polycyclic, fused, spiro or bridged carbocyclic ring systems. The term also includes polycyclic ring systems in which the carbocyclic ring can be "fused" to one or more non-aromatic carbocyclic or heterocyclic rings or one or more aromatic rings or combination thereof, wherein the radical or point of attachment is on the carbocyclic ring. "Fused" bicyclic ring systems comprise two rings which share two adjoining ring atoms. Bridged bicyclic group comprise two rings which share three or four adjacent ring atoms. Spiro bicyclic ring systems share one ring atom. Examples of cycloaliphatic groups include, but are not limited to, cycloalkyl and cycloalkenyl groups. Specific examples include, but are not limited to, cyclohexyl, cyclopropenyl, and cyclobutyl.

The term "heterocycle" (or "heterocyclyl", or "heterocyclic" or "non-aromatic heterocycle") as used herein refers to a non-aromatic ring system which can be saturated or contain one or more units of unsaturation, having three to fourteen ring atoms in which one or more ring carbons is replaced by a heteroatom such as, N, S, or O and each ring in the system contains 3 to 7 members. In some embodiments, non-aromatic heterocyclic rings comprise up to three heteroatoms selected from N, S and O within the ring. In other embodiments, non-aromatic heterocyclic rings comprise up to two heteroatoms selected from N, S and O within the ring system. In yet other embodiments, non-aromatic heterocyclic rings comprise up to two heteroatoms selected from N and O within the ring system. The term includes monocyclic, bicyclic or polycyclic fused, spiro or bridged heterocyclic ring systems. The term also includes polycyclic ring systems in which the heterocyclic ring can be fused to one or more non-aromatic carbocyclic or heterocyclic rings or one or more aromatic rings or combination thereof, wherein the radical or point of attachment is on the heterocyclic ring. Examples of heterocycles include, but are not limited to, piperidinyl, piperizinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, thiazocanyl, benzimidazolonyl, tetrahydrofuranyl, tetrahydrofuranyl, tetrahydrothiophenyl, tetrahydrothiophenyl, morpholino, including, for example, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolanyl, benzodithianyl, 3-(l-alkyl)-benzimidazol-2-onyl, and l,3-dihydro-imidazol-2-onyl.

As described herein, the immunogens may optionally be substituted with one or more substituents, such as illustrated generally below, or as exemplified by particular species of the invention. It will be appreciated that the phrase "optionally substituted" is used interchangeably with the phrase "substituted or unsubstituted." In general, the term "substituted", whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. When the term "optionally substituted" precedes a list, said term refers to all of the subsequent substitutable groups in that list.

Selection of substituents and combinations of substituents envisioned by this invention are those that result in the formation of stable or chemically feasible compounds. The term "stable", as used herein, refers to compounds that are not substantially altered when subjected to conditions to allow for their production, detection, and, specifically, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. Only those choices and combinations of substituents that result in a stable structure are contemplated. Such choices and combinations will be apparent to those of ordinary skill in the art and may be determined without undue experimentation.

Suitable substituents on a saturated or unsaturated carbon of an alkyl, alkene, cycloaliphatic, or heterocyclic ring are $C_1$-$C_6$ alkyl, halogen, cyano, oxo, —NCO, —ORb, —$SR^b$, —S(O)$R^a$, —SO$_2$$R^a$, —N$R^b$$R^c$, —C(O)$R^b$, —C(O)O$R^b$, —OC(O)$R^b$, —NRC(O)$R^b$, —C(O)N$R^b$$R^c$, —N$R^b$C(O) N$R^b$$R^c$, —N$R^b$C(O)O$R^b$, —OCON$R^b$$R^c$, —C(O) NRCO$_2$$R^b$, —N$R^b$C(O)N$R^b$C(O)O$R^b$, —C(O)NR(O$R^b$), —SO$_2$N$R^c$$R^b$, —N$R^b$SO$_2$$R^b$, —N$R^b$SO$_2$N$R^c$$R^b$, or —P(O) (O$R^a$)$_2$—; or two substituents join together with the atoms to which they are attached to form a 5-7-membered cycloalkyl or heterocyclic ring. Each $R^a$, $R^b$ and $R^c$ are each independently —H or $C_1$-$C_6$ alkyl. Other suitable substituents for a saturated carbon of an alkyl, alkene, cycloalkyl, or heterocyclic include the following: =O, =S, =NNHR*, =NN(R*)$_2$, =NNHC(O)R*, =NNHCO$_2$(alkyl), =NNHSO$_2$(alkyl), or =NR*, wherein each R* is independently selected from —H or C$_1$-C$_6$ alkyl.

Unless otherwise indicated, structures depicted herein are also meant to include all isomeric (e.g., enantiomeric, diastereomeric, cis-trans, conformational, and rotational) forms of the structure. For example, the R and S configurations for each asymmetric center, (Z) and (E) double bond isomers, and (Z) and (E) conformational isomers are included in this invention, unless only one of the isomers is drawn specifically. As would be understood to one skilled in the art, a substituent can freely rotate around any rotatable bonds. Therefore, single stereochemical isomers as well as enantiomeric, diastereomeric, cis/trans, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays. Such compounds, especially deuterium analogues, can also be therapeutically useful.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Combination Immunoassay Methods

O-desmethyltramadol is often found mixed with the psychoactive substance mitragynine (kratom), detection of the two substances, especially practical simultaneous detection, is also desirable, as this decreases the probability of a false negative result for drug detection compared to a single analyte assay when the two drugs of abuse are co-formulated; Krypton is a commercially available product which incorporates both O-desmethyltramadol and mitragynine. In one embodiment, the antibodies and immunoassay methods and kits for mitragynine (kratom), are as described in U.S. patent application Ser. No. 14/184,422, filed Feb. 19, 2014 entitled "Immunoassay for Detecting Kratom, its Constituents and their Use" the entire contents of which are incorporated herein by reference. In particular, U.S. patent application Ser. No. 14/184,422 describes a polyclonal antibody which that binds specifically to an epitope of one or more of mitragynine, 8-desmethylmitragynine, 8-sulphonylmitragynine, and 8-glucuronidylmitragynine which was raised to an immunogen having the structure of:

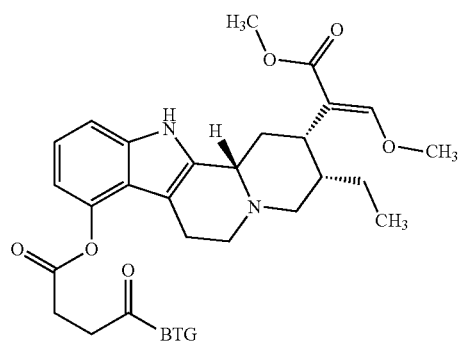

wherein "BTG" is bovine thyroglobulin,
wherein the polyclonal antibody has about 77.87% cross-reactivity to 8-desmethylmitragynine based on 100% cross-reactivity to mitragynine,
wherein the cross-reactivity of the polyclonal antibody is determined using a detecting agent having the structure of:

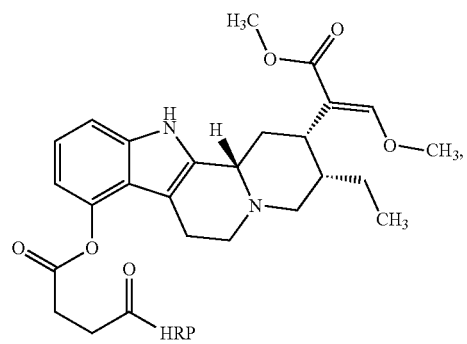

wherein HRP is horseradish peroxidase.
Thus the invention further describes:
An immunoassay method for detecting O-desmethyltramadol and/or mitragynine comprising bringing a sample suspected of containing O-desmethyltramadol and/or mitragynine into contact with two detecting agents and an antibody specific to O-desmethyltramadol and an antibody which binds to mitragynine in which one detecting agent competes with O-desmethyltramadol and the other detecting agent competes with mitragynine present in the sample for binding to their respective antibodies characterised in that the antibody specific to O-desmethyltramadol has a cross-reactivity of less than about 5% to tramadol and N-desmethyltramadol.
An immunoassay method for detecting O-desmethyltramadol and/or mitragynine, the method comprising contacting a solution or in vitro sample with two detecting agents and an antibody specific to O-desmethyltramadol and an antibody which binds to mitragynine characterised in that the antibody specific to O-desmethyltramadol has a cross-reactivity of less than about 5% to tramadol and N-desmethyltramadol compared with a cross-reactivity of about 100% for 0-desmethyltramadol.
In one embodiment, the present invention is an immunoassay method for detecting O-desmethyltramadol, the method comprising: i. contacting a solution or in vitro sample with a detecting agent and an antibody, wherein the antibody has a cross-reactivity of less than 5% to each of tramadol and N-desmethyltramadol compared with a cross-reactivity of 100% to O-desmethyltramadol; ii. detecting either the presence and/or amount of detecting agent bound to the antibody or the presence and/or amount of detecting agent not bound to the antibody; iii. determining the presence and/or amount of O-desmethyltramadol; iv. contacting the solution or in vitro sample with a second antibody, specific to mitragynine, and a second detecting agent; v. detecting the presence and/or amount of second detecting agent bound to the second antibody or the presence and/or amount of detecting agent not bound to the antibody; and vi. determining the presence and/or amount of O-desmethyltramadol; wherein steps i. and iv.; ii. and v.; and iii. and vi. take place simultaneously or sequentially in either order. That is, the two antibodies may be bound to the same surface and the sample or in vitro solution may contain both analytes to be detected, and the coulour changes in respond to the enzyme reacting with the substrates may be detected simultaneously.

A substrate comprising an antibody which binds specifically to O-desmethyl-tramadol and shows less than about 5% cross-reactivity to each of N-desmethyltramadol and tramadol compared to a cross-reactivity of about 100% to O-desmethyltramadol and an antibody specific to mitragynine. The substrate is preferably a ceramic biochip or a microtitre plate.

A kit comprising an antibody which binds specifically to O-desmethyltramadol and shows less than about 5% cross-reactivity to each of N-desmethyltramadol and tramadol compared to a cross-reactivity of about 100% to O-desmethyltramadol and an antibody which binds to mitragynine.

In preferred embodiments, the antibodies to mitragynine of the methods, kits and substrates have about 100% cross-reactivity to mitragynine and >about 10% cross-reactivity to 8-desmethylmitragynine; the cross-reactivity to 8-desmethylmitragynine is preferably between about 10% and about 90% compared to about 100% for mitragynine; the corresponding $IC_{50}$ of the antibodies for mitragynine is less than about 20 ng/ml, preferably less than about 10 ng/ml, more preferably less than about 5 ng/ml, most preferably less than about ing/ml.

Standard Reagents, Standard Methods, Examples and Results Standard Reagents/Methods
Haptens, Immunogens and Detecting Agents Use of the haptens, immunogens and detecting agents in connection with the current invention was supported by reference to Bioconjugate Techniques G. Hermanson, ed, Academic Press, 1996, 785 pp. In immunology, haptens are defined as substances which by themselves cannot elicit immune responses; they require chemical coupling to larger immunogenic molecules (antigenicity conferring carrier materials or 'accm'), to be capable of inducing an immune response. Appropriate accms commonly contain poly(amino acid) segments and include polypeptides, proteins and protein fragments. Illustrative examples of antigenicity conferring carrier materials are keyhole limpet haemocyanin (KLH), bovine thyroglobulin (BTG), bovine serum albumin (BSA), egg ovalbumin, bovine gamma globulin or cationised BSA. Alternatively, synthetic poly(amino acids) having a sufficient number of available amino groups, such as lysine, may be employed, as may other synthetic or natural polymeric materials bearing reactive functional groups. Also, carbohydrates, yeasts or polysaccharides may be conjugated to the hapten to produce an immunogen. The haptens can also be coupled to a detectable labelling agent such as an enzyme (for example, horseradish peroxidase), a substance having fluorescent properties or a radioactive label for the preparation of detecting agents for use in the immunoassays. The fluorescent substance may be, for example, a monovalent residue of fluorescein or a derivative thereof. Conjugation of haptens can be performed using standard methods of conjugation such as mixed anhydride, EDC or succinimidyl activation of the haptens. In order to confirm that adequate conjugation of hapten to carrier material has been achieved, prior to immunisation, each immunogen is evaluated using matrix-assisted UV laser desorption/ionisation time-of-flight mass spectroscopy (MALDI-TOF MS).
General Procedure for MALDI-TOF Analysis of Immunogens MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 µl) were analysed using a matrix of sinapinic acid and bovine serum albumin (Fluka) was used as an external calibrant.

Preparation of Antisera

Pre-immunization blood samples are collected from sheep. In order to generate polyclonal antisera, 2 mgs of the immunogen (structure 1) is prepared in PBS, mixed at a ratio of 50% immunogen in PBS to 50% Freund's Complete adjuvant (Sigma, Product Number F5881) and emulsified by repeatedly passing the mixture through a tip on the end of a 1 ml syringe, until it reaches the required semi-solid consistency. 1.1 ml of the emulsified mixture is injected intramuscularly into each host animal (sheep) as the primary immunisation dose. Further injections (boosts) are prepared (1 mg of immunogen is prepared in PBS and mixed at a ratio of 50% Immunogen in PBS/50% Freunds Incomplete adjuvant, Sigma, Product Number—F5506). Boost injections are delivered intramuscularly at monthly intervals, 1 ml per animal. Serum is sampled monthly by collection of whole blood from the jugular vein for evaluation of the antibody titre. The degree of antibody purification required depends on the intended application. For many purposes, there is no requirement for purification of the serum, however, in other cases, such as, where the antibody is to be immobilised on a solid support, purification steps (such as caprylic acid/ammonium sulphate precipitation) can be taken to remove undesired material and eliminate non-specific binding. In another embodiment, the purification is by immunoglobulin precipitation, antigen-specific affinity purification, column chromatography, such as, size-exclusion chromatography or ion exchange chromatography.

Immunoassay Development

The process of developing an immunoassay is well known to the person skilled in the art. A detecting agent (e.g. hapten conjugated to detectable label) is added to a sample containing the target analyte and the raised antibodies, and the detecting agent and analyte compete for binding to the antibodies. The antibodies located at the surface of a suitable solid support; dilution of antibodies in coating buffer and incubation can enable antibody attraction to a suitable surface or their binding to a chemically activated surface. The antibodies can be polyclonal or monoclonal using standard techniques. The signal emitted in the immunoassay is proportionate to the amount of detecting agent bound to the antibodies which in turn is inversely proportionate to the analyte concentration. The signal can be detected or quantified by comparison with a calibrator with known levels of target analyte.

Enzyme Immunoassays, ELISAs

The enzyme-linked immunosorbent assay (ELISA) is a test that uses antibodies and colour change to identify a substance.

Performing an ELISA involves at least one antibody with specificity for a particular antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody that is linked to an enzyme through bioconjugation. Between each step, the plate is typically washed to remove any proteins or antibodies that are not specifically bound. After the final wash step, the plate is developed by adding an enzyme to produce a visible signal, which indicates the quantity of antigen in the sample.

Lateral Flow Devices

In recent years, the in vitro diagnostics industry has made enormous efforts to develop immunochromatographic tests. Such tests have found applications in both clinical and non-clinical fields. A clinical utility of this test format is particularly suited to point of care utilities.

Rapid immunochromatographic test devices, e.g. in the form of a test strip, are made up of a number of components. Such a test strip commonly includes a sample pad, a conjugate pad, a membrane, e.g. a nitrocellulose membrane, and an absorbent pad. The membrane is usually attached by means of an adhesive to a supporting backing, e.g. made of plastic. In practice, the user dispenses a patient sample (such as urine or whole blood) onto the sample pad. The sample then flows through the sample pad into the conjugate pad, where it mixes with, and releases, the detector reagent. This mixture then flows across the membrane, where it binds with the test and control reagents located in the capture test zone (sample zone) and negative control zone, respectively. When the mixture binds to the reagent that forms the test line, a positive result is indicated. The colour intensity of the test line is proportional to the concentration of analyte in the sample. Excess sample that flows beyond the test and control zones is taken up in the absorbent pad.

Rapid immunochromatographic test devices for diagnostic purposes are easy to operate and thus do not only contribute to the comfort of professional users, e.g. medical stuff, but also allow the operation by non-professional users, e.g. most patients.

EXAMPLES

Example 1: Preparation of 2-[(dimethylamino) methyl]cyclohexan-1-one 2

A solution containing cyclohexanone 1 (30.9 ml, 0.29 mol), paraformaldehyde (10.8 g, 0.36 mol, 1.2 eq), dimethylamine hydrochloride (24.48 g, 0.3 mol, 1 eq), conc. hydrochloric acid (1.2 ml) and ethanol (12 ml) was heated at reflux for 4 hours resulting in a black solution. The solvents were removed in vacuo and the resulting residue was dissolved in ethanol (120 ml). Acetone (330 ml) was added resulting in a white precipitate. The precipitate was recovered by filtration to gave 2-[(dimethylamino)methyl] cyclohexan-1-one hydrochloride (26 g) as white solid (mp 153-154° C.). This was then dissolved in water (200 ml) and sodium bicarbonate was added portionwise to the solution until pH remained basic. The mixture was stirred for 1 hour at RT and then extracted with chloroform (3×200 ml). The organic extracts were combined, dried over sodium sulfate, filtered and evaporated to dryness to give the title compound 2 (free base) (13 g) as a yellow oil.

Example 2: Preparation of 3-(benzyloxy)phenyl bromide 3

To a mixture of 3-bromophenol (20 g, 0.115 mol) and potassium carbonate (95 g, 0.69 mol, 6 eq) in acetone (500 ml) was added benzyl bromide (15.12 ml, 0.127 mol, 1.1 eq). The reaction mixture was heated at reflux for 2 hours (TLC showed completion of reaction). The reaction mixture was filtered, washed with acetone and the filtrate was evaporated to dryness. The residue was dissolved in water (200 ml) and ethyl acetate (200 ml). The layers were separated. The organic layer was washed with brine (200 ml), dried over sodium sulfate, filtered and evaporated to dryness. The crude was recrystallized from hexane to give the title compound (26 g) 3 as a white solid. MP 61-62° C.

Example 3: Preparation of 1-(3-(benzyloxy)phenyl)-2-((dimethylamino)methyl)cyclohexan-1-ol 4

To a suspension of magnesium (6 g, 0.25 mol, 3 eq) in dry diethyl ether (30 ml) was added iodine crystal followed by a solution of 3-(benzyloxy)phenyl bromide 3 (22 g, 83.7 mmol) in dry tetrahydrofuran (50 ml) dropwise at a rate (once reaction has initiated), under a nitrogen atmosphere, maintaining a gentle reflux. The resulting mixture was heated at reflux for 1 hour. The mixture was cooled to 0° C. and a solution of 2-[(dimethylamino)methyl]cyclohexan-1-one 2 (13 g, 83.7 mmol, 1 eq) in dry tetrahydrofuran (50 ml) was added dropwise. The reaction mixture was stirred for 4 hours at RT (room temperature). The reaction mixture was cooled at 0° C. and an aqueous solution of ammonium chloride was added dropwise and the resulting suspension was stirred at room temperature overnight. The mixture was filtered through a pad of Celite™ and washed with ethyl acetate (3×200 ml). The extracts were combined, washed with brine, dried over sodium sulfate, filtered and evaporated to dryness. The residue obtained was purified by column chromatography (silica gel; 0-50% ethyl acetate in hexane) to give the title compound (15.75 g) 4 as a yellow oil.

Example 4: Preparation of 1-(3-(benzyloxy)phenyl)-2-((methylamino)methyl) cyclohexan-1-ol 5

A solution of 1-(3-(benzyloxy)phenyl)-2-((dimethylamino)methyl) cyclohexan-1-ol 4 (4 g, 11.8 mmol) and diethylazodicarboxylate (DEAD, 2.4 ml, 15.3 mmol, 1.3 eq) in toluene (50 ml) was heated at 55° C. overnight (O/N). The solvent was removed in vacuo and the residue was dissolved in ethanol (15 ml) and a saturated solution of ammonium chloride (15 ml) was added. The mixture was heated at reflux for 2 hours. The solvent was evaporated and the residue was dissolved in ethyl acetate (20 ml), water (20 ml) and a 10% aqueous solution of potassium carbonate (10 ml). The layers were separated and the aqueous layer was extracted with ethyl acetate (3×50 ml). The extracts were combined, dried over sodium sulfate, filtered and evaporated to dryness. The residue obtained was purified by column chromatography (silica gel; 0-10% methanol in chloroform containing TEA) to give the title compound (1.28 g) 5 as a white solid.

Example 5: Preparation of N-Carboethoxypropyl-1-(3-(benzyloxy)phenyl)-2-((methylamino)methyl) cyclohexan-1-ol (1-(3-(benzyloxy)phenyl)-2-((methyl(Carboethoxypropyl)amino)methyl) cyclohexan-1-ol, ethyl 4-(((2-(3-(benzyloxy)phenyl)-2-hydroxycyclohexyl)methyl)(methyl)amino) butanoate) 6

A solution containing 1-(3-(benzyloxy)phenyl)-2-((methylamino)methyl) cyclohexan-1-ol 5 (1.28 g, 3.93 mmol), potassium carbonate (1.19 g, 8.65 mmol, 2.2 eq) and ethyl 4-bromobutyrate (843 ul, 5.89 mmol, 1.5 eq) in dimethylformamide (DMF, 20 ml) were stirred at room temperature overnight. The reaction mixture was filtered and the filtrate was evaporated to dryness. The crude residue obtained was purified by column chromatography (silica gel; 0-50% ethyl acetate in hexane) to give the title compound (1 g) 6 as solid.

Example 6: Preparation of N-Carboxypropyl-1-(3-(benzyloxy)phenyl)-2-((methylamino)methyl) cyclohexan-1-ol (1-(3-(benzyloxy)phenyl)-2-((methyl(Carboxypropyl)amino)methyl) cyclohexan-1-ol, 4-(((2-(3-(benzyloxy)phenyl)-2-hydroxycyclohexyl)methyl)(methyl)amino)butanoic acid) 7

To a solution of N-Carboethoxypropyl-1-(3-(benzyloxy)phenyl)-2-((methylamino)methyl) cyclohexan-1-ol 6 (1 g, 2.27 mmol) in tetrahydrofuran (20 ml) at room temperature was added dropwise a solution of potassium hydroxide (449 mg, 6.82 mmol, 3 eq) in water (20 ml) and the resulting reaction mixture was stirred at room temperature overnight. A solution of aqueous (3M) HCl was added to bring the pH of the reaction to 3 and the reaction mixture was extracted with ethyl acetate (3×50 ml). The extracts were combined, dried over sodium sulfate, filtered and evaporated to dryness. The crude residue obtained was purified by column chromatography (silica gel; 0-10% methanol in chloroform) to give the title compound (690 mg) 7 as a white solid.

Example 7: Preparation of N-Carboxypropyl-3-(2-((methylamino)methyl)-1-hydroxycyclohexyl) phenol 3-(2-((methyl(carboxypropyl)amino)methyl)-1-hydroxycyclohexyl) phenol, 4-(((2-hydroxy-2-(3-hydroxyphenyl)cyclohexyl)methyl)(methyl)amino) butanoic acid) (Hapten)

Through a solution containing N-Carboxypropyl-1-(3-(benzyloxy)phenyl)-2-((methylamino)methyl) cyclohexan-1-ol 7 (690 mg, 1.67 mmol) and 5% palladium on charcoal (240 mg) in ethanol (50 ml) at room temperature was bubbled hydrogen gas via a balloon until TLC showed completion of reaction. The reaction mixture was filtered through a pad of Celite™ and the solvent was evaporated in vacuo. The crude residue obtained was purified by column chromatography (silica gel; 0-20% methanol in chloroform) to give the title compound (455 mg) as a white amorphous solid (Hapten). The structure was confirmed by NMR analysis (See FIG. 4).

Example 8: Conjugation of N-Carboxypropyl-3-(2-((methylamino)methyl)-1-hydroxycyclohexyl) phenol (Hapten) to BSA (Immunogen-1)

To a solution of N-Carboxypropyl-3-(2-((methylamino) methyl)-1-hydroxycyclohexyl) phenol (Hapten) (24.8 mg) in DMF (1.0 ml) was added N-(3-Dimethylaminopropyl)-N'-ethylcarbodiimide hydrochloride EDC. HCl (73.8 mg) and N-hydroxysuccinimide (44.2 mg) and the mixture was incubated on the roller at room temperature overnight. This solution was added dropwise to a solution of BSA (100 mg, 1.5 µmol) in phosphate buffer saline (50 mM) (pH 8.0) (10 ml). The resulting solution was incubated on the roller at room temperature overnight. Excess hapten was removed by dialysis against phosphate buffer saline, pH 7.2 (3 changes) for 24 hours at 4° C., and freeze-dried. MALDI results showed 13.0 molecule of N-Carboxypropyl-3-(2-((methylamino)methyl)-1-hydroxycyclohexyl) phenol (Hapten) had been conjugated to one molecule of BSA. The Hapten is directly linked to BSA without a linking group.

Example 9: Conjugation of N-Carboxypropyl-3-(2-((methylamino)methyl)-1-hydroxycyclohexyl) phenol (Hapten) to KLH (Immunogen-2)

To a solution of N-Carboxypropyl-3-(2-((methylamino) methyl)-1-hydroxycyclohexyl) phenol (Hapten) (24.7 mg) in DMF (1.0 ml) was added N-(3-Dimethylaminopropyl)-N'-ethylcarbodiimide hydrochloride EDC.HCl (73.7 mg) and N-hydroxysuccinimide (44.3 mg) and the mixture was incubated on the roller at room temperature overnight. This solution was added dropwise to a solution of KLH (100 mg) in phosphate buffer saline (50 mM) (pH 8.0) (10 ml). The resulting solution was incubated on the roller at room temperature overnight. Excess hapten was removed by dialysis against phosphate buffer saline, pH 7.2 (3 changes) for 24 hours at 4° C., and freeze-dried. The Hapten is directly linked to KLH without a linking group.

Example 10: Conjugation of N-Carboxypropyl-3-(2-((methylamino)methyl)-1-hydroxycyclohexyl) phenol (Hapten) to HRP (Tracer-1)

EDC hydrochloride (1.5 mg) was dissolved in water (0.5 ml) and immediately added to a solution of N-Carboxypropyl-3-(2-((methylamino)methyl)-1-hydroxycyclohexyl) phenol (Hapten) (3 mg) in DMF (0.2 ml). After mixing, this solution was added dropwise to a solution of HRP (20 mg) in water (1 ml). N-hydroxysuccinimide (1 mg) was added and the reaction mixture was incubated in the dark at room temperature overnight. Excess hapten was removed with double PD-10 columns (Pharmacia) in series, pre-equilibrated with PBS at pH 7.2. The hapten-1-HRP conjugate (Tracer-1) was then dialysed overnight against 10 L of PBS at pH 7.2 at 4° C. The Hapten is directly linked to HRP without a linking group.

Example 11: Immunoassay Development

The polyclonal antibody raised against Immunogen-2 of Example 9 was removed from fridge or freezer and brought to room temperature. The antibody was diluted to 2.5 µg/ml in 10 mM Tris pH 8.5 and all appropriate wells are coated at 125 µl/well at 37° C. for 2 hours or at 4° C. overnight. The plate was washed 4 times over a period of 10 minutes with working strength tris-buffered saline and tween 20 (TBST) wash buffer and tapped dry. 50 µl of working strength TBST was pipetted into the appropriate wells. Dilutions of target analyte and potential crossreactant(s) were prepared in working strength TBST and pipetted (50 µl) into the appropriate wells beginning with the lowest concentration to the highest concentration. Hapten-HRP (Tracer-1) conjugate at the appropriate concentration was prepared in conjugate dilution buffer and 75 µl into pipetted into appropriate wells. The plate was tapped gently to mix contents, sealed and incubated at 25° C. for 1 hour. The plate was washed 6 times over a 10-15 minute period (3 quick washes followed by 3 additional washes over 12 minutes) and tapped dry thoroughly onto tissue paper. Trimethylbenzidine (TMB) solution (125 μl) was added to each well and tapped gently, and the plate was incubated at room temperature for 20 minutes in the dark. The reaction was stopped by addition of 125 μl of 0.2 M sulphuric acid to each well and the absorbance measured at 450 nm using an ELISA plate reader (Biotek Elx800).

Results

TABLE 2

ELISA data for an antibody raised against Immunogen-2 using Tracer-1 as detecting agent for tramadol and metabolites

| | O-Desmethyltramadol | | N-Desmethyltramadol | | Tramadol | |
|---|---|---|---|---|---|---|
| ng/ml | $A_{450}$ | B/Bo | $A_{450}$ | B/Bo | $A_{450}$ | B/Bo |
| 0.000 | 1.969 | 100 | 1.934 | 100 | 1.909 | 100 |
| 0.156 | 1.049 | 53 | 1.884 | 97 | 1.858 | 97 |
| 0.313 | 0.735 | 37 | 1.891 | 98 | 1.782 | 93 |
| 0.625 | 0.479 | 24 | 1.917 | 99 | 1.792 | 94 |
| 1.250 | 0.308 | 16 | 1.930 | 100 | 1.786 | 94 |
| 2.500 | 0.193 | 10 | 1.908 | 99 | 1.819 | 95 |
| 5.000 | 0.122 | 6 | 1.885 | 97 | 1.793 | 94 |
| 10.000 | 0.076 | 4 | 1.896 | 98 | 1.786 | 94 |
| $IC_{50}$ ng/ml | 0.178 | | >>10 | | >>10 | |
| % CR | 100 | | <<1.78 | | <<1.78 | |

A total of three sheep were immunised with Immunogen-2 and produced antibodies with $IC_{50}s$ to O-desmethyltramadol of 0.178 ng/ml, 0.181 ng/ml and 0.214 ng/ml while displaying no cross-reactivity to N-desmethyltramadol and tramadol. Table 2 shows that, for N-desmethyltramadol and tramadol, there is no appreciable binding as the B/Bo remains constant with no decrease in absorbance at the concentrations tested.

TABLE 3

ELISA data for mitragynine and 8-desmethylmitragynine

| | Mitragynine | | | 8-Desmethylmitragynine | | |
|---|---|---|---|---|---|---|
| ng/ml | $A_{450}$ | % CV | B/Bo | $A_{450}$ | % CV | B/Bo |
| 0.000 | 1.612 | 4.1 | 100 | 1.510 | 1.0 | 100 |
| 0.313 | 1.216 | 6.4 | 75 | 1.116 | 6.0 | 74 |
| 0.625 | 1.012 | 6.3 | 63 | 0.956 | 4.6 | 63 |
| 1.250 | 0.787 | 7.2 | 49 | 0.816 | 2.7 | 54 |
| 2.500 | 0.590 | 10.9 | 37 | 0.633 | 3.7 | 42 |
| 5.000 | 0.401 | 10.1 | 25 | 0.441 | 1.4 | 29 |
| 10.000 | 0.273 | 7.5 | 17 | 0.279 | 3.2 | 18 |
| 20.000 | 0.177 | 13.1 | 11 | 0.191 | 2.4 | 13 |
| $IC_{50}$ ng/ml | | 1.193 | | | 1.532 | |
| % CR | | 100.00 | | | 77.87 | |

$A_{450}$ = absorbance at 450 nm; B = absorbance at 450 nm at x ng/ml calibrator concentration; $B_0$ = absorbance at 450 nm at 0 ng/ml calibrator concentration; $IC_{50}$ = standard concentration which produces 50% $B/B_0$; % CR = percentage cross-reactivity based on 100% specificity to mitragynine.
% CR = IC50 ng/ml (cross-reactant at 100%)/IC50 ng/ml (cross-reactant) × 100

The binding characteristics of the antibody enable a highly sensitive and specific assay for O-desmethyltramadol; these characteristics also enable an assay for krypton detection.

STATEMENTS OF THE INVENTION

1. An immunoassay method for detecting O-desmethyltramadol comprising bringing a sample suspected of containing O-desmethyltramadol into contact with a detecting agent and an antibody specific to O-desmethyltramadol, in which the detecting agent competes with O-desmethyltramadol present in the sample for binding to the antibody, characterised in that the antibody specific to O-desmethyltramadol has a cross-reactivity of less than 5% to each of tramadol and N-desmethyltramadol.

2. The immunoassay method of statement 1 in which the antibody has an $IC_{50}$ of less than or about 1 ng/ml to O-desmethyltramadol.

3. The immunoassay method of the preceding statements in which the antibody specific to O-desmethyltramadol is located at the surface of a substrate.

4. The immunoassay method of statement 3 in which the substrate is a microtitre plate, a bead, a slide or a biochip.

5. The immunoassay method of the preceding statements which also comprises detecting mitragynine and further incorporates an antibody specific to mitragynine and a further detecting agent which competes with mitragynine present in the sample for binding to the antibody specific to mitragynine.

6. The immunoassay methods of any of the preceding statements in which the antibodies specific to O-desmethyltramadol are derived from an immunogen of structure

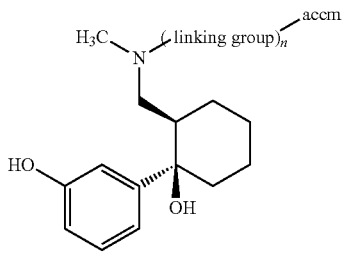

In which n=0 or 1 and the accm is an antigenicity conferring carrier material.

7. An antibody which binds specifically to O-desmethyltramadol and shows less than 5% cross-reactivity to each of N-desmethyltramadol and tramadol compared to a cross-reactivity of 100% to O-desmethyltramadol.

8. The antibody of statement 7 further characterised by having an $IC_{50}$ of less than or about 1 ng/ml to O-desmethyltramadol.

9. The antibody of either of statements 7 or 8 which is derived from an immunogen of structure

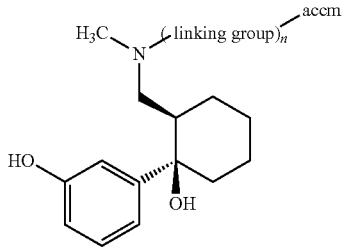

in which n=0 or 1 and the accm is an antigenicity conferring carrier material.

10. A substrate comprising an antibody as described in statements 7 to 9.

11. The substrate of statement 10 which further comprises an antibody which binds to mitragynine.

12. The substrate of statements 10 and 11 which is a ceramic biochip or a microtitre plate.

13. A kit comprising an antibody as described in statements 7 to 9.

14. The kit of statement 13 which further comprises an antibody which binds to mitragynine.

The invention claimed is:

1. A polyclonal antibody that binds specifically to an epitope of O-desmethyltramadol, which polyclonal antibody was raised to an immunogen having the structure of:

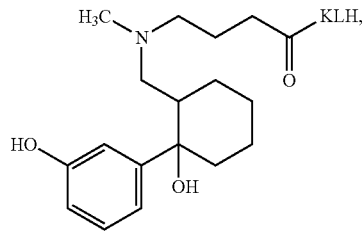

wherein KLH is keyhole limpet hemocyanin, wherein the polyclonal antibody has less than 1.78% cross-reactivity to each of N-desmethyltramadol and tramadol compared to a cross-reactivity of 100% to O-desmethyltramadol, wherein the cross-reactivity is determined using a detecting agent having the structure of:

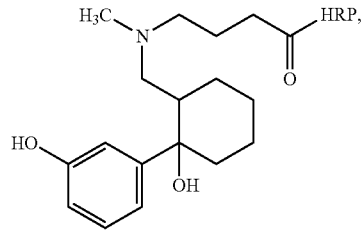

wherein HRP is horseradish peroxidase.

2. A substrate comprising the polyclonal antibody as described in claim 1.

3. The substrate of claim 2, further comprising a polyclonal antibody that binds specifically to an epitope of one or more of mitragynine, 8-desmethylmitragynine, 8-sulphonylmitragynine, and 8-glucuronidylmitragynine, which polyclonal antibody was raised to an immunogen having the structure of:

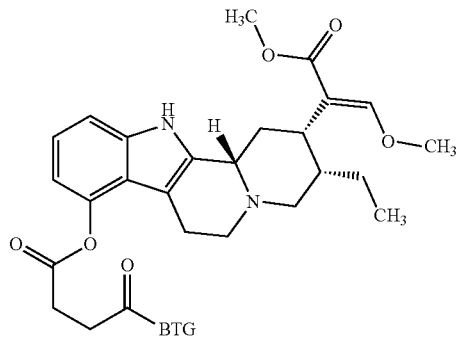

wherein "BTG" is bovine thyroglobulin, wherein the polyclonal antibody has about 77.87% cross-reactivity to 8-desmethylmitragynine based on 100% cross-reactivity to mitragynine, wherein the cross-reactivity of the polyclonal antibody is determined using a detecting agent having the structure of:

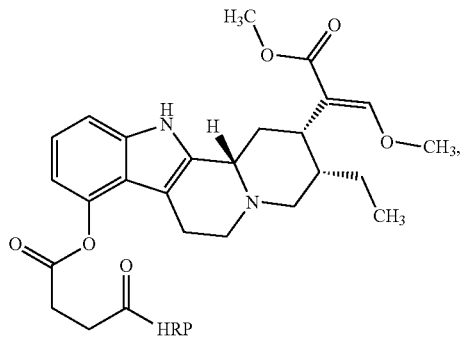

wherein HRP is horseradish peroxidase.

4. The substrate of claim 2, which is a ceramic biochip or a microtitre plate.

5. A kit comprising the polyclonal antibody as described in claim 1.

6. The kit of claim 5, further comprising a polyclonal antibody that binds specifically to an epitope of one or more of mitragynine, 8-desmethylmitragynine, 8-sulphonylmitragynine, and 8-glucuronidylmitragynine, which polyclonal antibody was raised to an immunogen having the structure of:

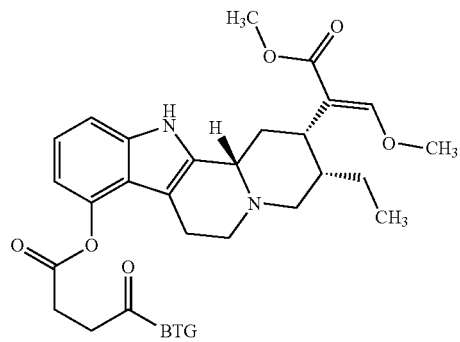

wherein "BTG" is bovine thyroglobulin, wherein the polyclonal antibody has about 77.87% cross-reactivity to 8-desmethylmitragynine based on 100% cross-reactivity to mitragynine, wherein the cross-reactivity of the polyclonal antibody is determined using a detecting agent having the structure of:

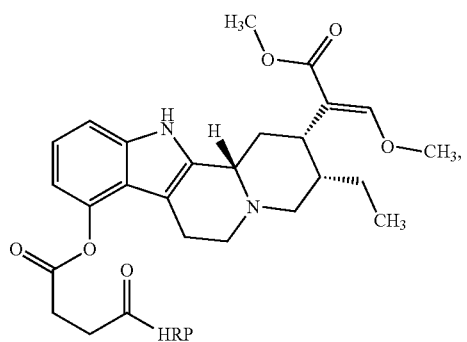
wherein HRP is horseradish peroxidase.
* * * * *